(12) United States Patent
Jung et al.

(10) Patent No.: US 10,845,350 B2
(45) Date of Patent: Nov. 24, 2020

(54) HYDROGEN SENSOR PRODUCTION METHOD AND HYDROGEN SENSOR PRODUCED THEREBY

(71) Applicant: GWANGJU INSTITUTE OF SCIENCE AND TECHNOLOGY, Gwangju (KR)

(72) Inventors: Gunyoung Jung, Gwangju (KR); Yusin Pak, Gwangju (KR)

(73) Assignees: GWANGJU INSTITUTE OF SCIENCE AND TECHNOLOGY; Renaissance IP Law Group LLP

( * ) Notice: Subject to any disclaimer, the term of this patent is extended or adjusted under 35 U.S.C. 154(b) by 391 days.

(21) Appl. No.: 15/766,803

(22) PCT Filed: Aug. 19, 2016

(86) PCT No.: PCT/KR2016/009200
§ 371 (c)(1),
(2) Date: Sep. 10, 2018

(87) PCT Pub. No.: WO2017/030421
PCT Pub. Date: Feb. 23, 2017

(65) Prior Publication Data
US 2019/0011412 A1 Jan. 10, 2019

(30) Foreign Application Priority Data
Aug. 19, 2015 (KR) .................... 10-2015-0116799

(51) Int. Cl.
*G01N 33/00* (2006.01)
*H01L 21/28* (2006.01)
*B82Y 15/00* (2011.01)

(52) U.S. Cl.
CPC .......... *G01N 33/005* (2013.01); *H01L 21/28* (2013.01); *B82Y 15/00* (2013.01)

(58) Field of Classification Search
CPC ........ G01N 33/005; H01L 21/28; B82Y 15/00
See application file for complete search history.

(56) References Cited

U.S. PATENT DOCUMENTS 6,410,416 B1 * 6/2002 Dodabalapur ........ H01S 5/1231
385/135
6,946,332 B2 * 9/2005 Loo ........................ B82Y 10/00
257/E27.112

(Continued)

OTHER PUBLICATIONS

Kyeongmi Lee et al. "Nonaqueous nanoscale metal transfer by controlling the stickiness of organic film", Langmuir, vol. 24, pp. 8413-8416 (Year: 2008).*

(Continued)

*Primary Examiner* — Natalie Huls
(74) *Attorney, Agent, or Firm* — Renaissance IP Law Group LLP

(57) ABSTRACT

The present invention provides a method of manufacturing a hydrogen sensor and a hydrogen sensor manufactured thereby. Specifically, the method according to the present invention includes a step of forming a self-assembled single layer on a stamp substrate provided with nanoline-patterned uneven parts; a step of depositing a metal thin film layer on the self-assembled single layer; a step of disposing the stamp substrate on a flexible sensor substrate so that a polymer layer formed on the sensor substrate and the metal thin film layer deposited on the uneven parts are brought into contact with each other; a step of transferring a metal nanoribbon array having nanogaps to the sensor substrate by performing pressure and heat treatment on the stamp substrate and removing the stamp substrate; and a step of forming first and second electrodes on both ends of the transferred metal nanoribbon array.

17 Claims, 4 Drawing Sheets

(56) References Cited

U.S. PATENT DOCUMENTS

| | | | | |
|---|---|---|---|---|
| 2004/0121568 A1* | 6/2004 | Kim | ............... | B33Y 10/00 |
| | | | | 438/584 |
| 2005/0170621 A1* | 8/2005 | Kim | ............... | B33Y 10/00 |
| | | | | 438/584 |
| 2007/0215480 A1* | 9/2007 | Fang | ............... | C25D 17/007 |
| | | | | 205/118 |
| 2009/0050487 A1* | 2/2009 | Fang | ............... | C25D 17/007 |
| | | | | 205/135 |
| 2009/0084159 A1* | 4/2009 | Sun | ............... | G01N 27/127 |
| | | | | 73/31.05 |
| 2010/0108529 A1* | 5/2010 | Zamborini | ............... | G01N 33/005 |
| | | | | 205/205 |
| 2011/0045601 A1* | 2/2011 | Gryska | ............... | G01N 27/221 |
| | | | | 436/149 |
| 2014/0152579 A1* | 6/2014 | Frey | ............... | G06F 3/041 |
| | | | | 345/173 |
| 2015/0362470 A1* | 12/2015 | Jung | ............... | C01B 32/05 |
| | | | | 73/31.05 |
| 2016/0250875 A1* | 9/2016 | Tarnowski | ............... | B41K 1/38 |
| | | | | 345/173 |

OTHER PUBLICATIONS

Jae Won Jeong et al. "High resolution nanotransfer printing applicable to diverse surfaces via interface-targeted adhesion switching", Nature Communications, 6387, pp. 1-9 (Year: 2014).*

Byungjin Jang et al. "Palladium nanogap-based H2 sensors on a patterned elastomeric substrate using nanoimprint lithography", Sensors and Actuators B: Chemical, vol. 221, pp. 593-598. (Year: 2015).*

* cited by examiner

HYDROGEN SENSOR PRODUCTION METHOD AND HYDROGEN SENSOR PRODUCED THEREBY

TECHNICAL FIELD

The present invention relates to a hydrogen sensor, and more particularly, to a method of manufacturing a hydrogen sensor including a metal nanoribbon array and a hydrogen sensor manufactured thereby.

BACKGROUND ART

In recent years, there is growing interest in using hydrogen as an energy resource to cope with environmental pollution and depletion of fossil energy reserves. Accordingly, commercialization of hydrogen energy has been actively carried out in various fields. In general, since hydrogen may spontaneously ignite when combined with oxygen in the atmosphere and may explode at a concentration of 4% or more, caution is required when producing, storing, and using hydrogen. Therefore, research on a hydrogen detection sensor capable of detecting hydrogen leaks is being carried out.

To date, commercially available gas sensors include optical analysis-based non-dispersive infrared (NDIR) sensors and metal oxide sensors using $ZnO$, $SnO_2$, $TiO_2$, or the like. Since the NDIR sensor includes an IR source, a detector, an analyzer, and a chamber, a structure thereof is large and manufacturing costs thereof are high. The metal oxide sensor has a very simple structure, but does not normally operate at room temperature, and thus is used in combination with a heater capable of applying heat of about 400° C. or more to the sensor. However, since a metal oxide sensor to which a heater is coupled has a high driving power, there is a limitation in practical applications such as miniaturized sensors. In addition, a response time required for processing an analysis signal for analyzing the characteristics of the gas from the time of exposing a metal oxide is long, and recovery time for recovering the reaction is also long. In addition, long-term use of the metal oxide sensor is limited because the surface of the metal oxide sensor easily cracks or is lifted due to repeated gas inflow and outflow.

DISCLOSURE

Technical Problem

The present invention is directed to providing a method of manufacturing a hydrogen sensor and the hydrogen sensor having excellent operating characteristics and high sensitivity at room temperature.

Technical Solution

One aspect of the present invention provides a method of manufacturing a hydrogen sensor, including a step of forming a self-assembled single layer on a stamp substrate provided with uneven parts for pattern formation; a step of forming a metal thin film layer on the self-assembled single layer; a step of disposing the stamp substrate on a sensor substrate so that a polymer layer formed on the sensor substrate and the metal thin film layer are brought into contact with each other; a step of transferring a metal nanoribbon array having nanogaps to the sensor substrate by performing pressure and heat treatment on the stamp substrate and removing the stamp substrate; and a step of respectively forming first and second electrodes on both ends of the metal nanoribbon array.

The self-assembled single layer may be formed of at least one material selected from tridecafluoro-1,1,2,2-tetrahydrooctyltrichlorosilane, octadecyltrichlorosilane, 3-methacryloxypropyltrimethoxysilane, and 3-aminopropyltriethoxysilane, and the metal thin film layer may be formed of any one selected from palladium (Pd), platinum (Pt), nickel (Ni), gold (Au), silver (Ag), titanium (Ti), cobalt (Co), tungsten (W), and an alloy of two or more thereof.

The metal thin film layer may be formed using at least one method selected from electron beam evaporation, thermal evaporation, and sputtering, and the metal thin film layer may be formed to have a thickness of 5 nm to 30 nm.

Any one material having flexibility selected from polyethylene terephthalate (PET), polyethylene naphthalate (PEN), polyethersulfone (PES), polyimide (PI), and polyvinyl chloride (PVC) may be used to be the sensor substrate, and the polymer layer formed on the sensor substrate may include at least one material selected from polymethyl methacrylate (PMMA), polyacrylonitrile (PAN), polyethylene oxide (PEO), and polyvinylidene difluoride (PVDF).

When the metal nanoribbon array is transferred, the stamp substrate may be heat-treated at a temperature of 100° C. to 200° C. under a pressure of 100 psi to 200 psi.

The first and second electrodes may be formed in parallel with the alignment direction of the nanogaps.

The method of the present invention may further include a step of bending the sensor substrate upward in a convex shape, and, when the bending process is performed, the sensor substrate may be bent to have a bending radius of 1 mm to 3 mm.

Another aspect of the present invention provides a hydrogen sensor including a substrate on which a pattern is formed; a polymer layer disposed on the substrate and having a pattern corresponding to the pattern of the substrate; a metal nanoribbon array disposed on the polymer layer and having a pattern corresponding to the pattern of the polymer layer, wherein the metal nanoribbon array has nanogaps; and first and second electrodes formed on both ends of the metal nanoribbon array, respectively.

The first and second electrodes may be arranged in a direction parallel to the alignment direction of the nanogaps.

The nanogaps may have a width of 1 nm to 80 nm.

The metal nanoribbon array may have a thickness of 5 nm to 30 nm, and the width between the first and second electrodes may be 200 μm to 4,000 μm.

The sensor substrate may be subjected to a bending process so that the sensor substrate is bent upward in a convex shape.

Advantageous Effects

According to the method of manufacturing a hydrogen sensor, since a metal nanoribbon array can be directly transferred to a substrate without a lithography process using an organic solvent, substrates susceptible to organic solvents can be used.

In addition, since a method of directly transferring a metal is used, a metal nanoribbon array having nanogaps can be easily formed in a polymer thin film by a single process.

In addition, since resistance between the electrodes is increased due to the nanogaps formed in the metal nanoribbon array of the present invention, initial current can be reduced, thereby increasing the operation speed and sensitivity of the hydrogen sensor.

In addition, according to the hydrogen sensor of the present invention, bending of the sensor substrate can expand the nanogaps to further reduce the initial current, thereby improving performance of the sensor.

The effects of the present invention are not limited to the effects mentioned above, and other effects not mentioned can be clearly understood by those skilled in the art from the following description.

BEST MODE

Figure 1:
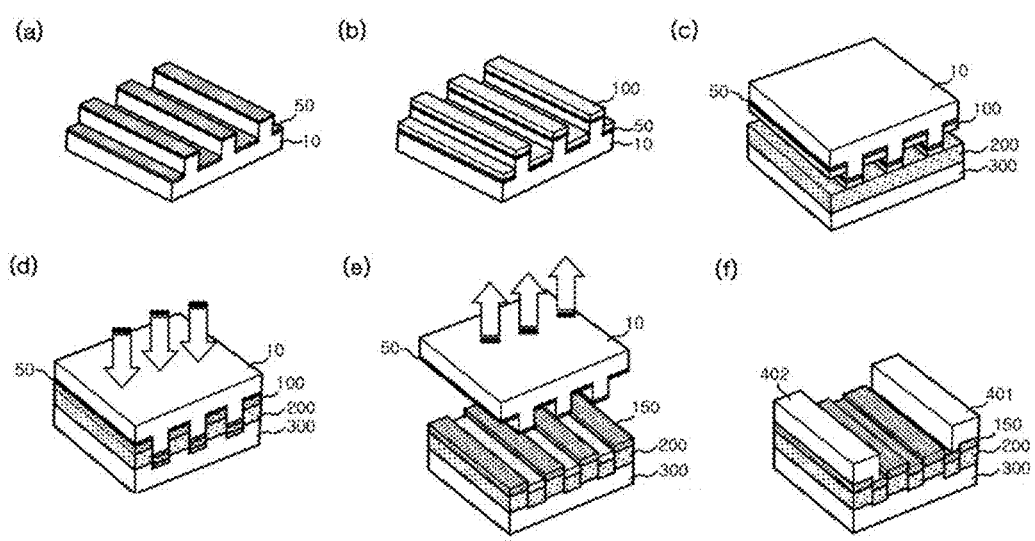
FIGS. 1a-1f include schematic diagrams illustrating a method of manufacturing a hydrogen sensor according to one embodiment of the present invention.

Hereinafter, embodiments of the present invention will be described in detail with reference to the accompanying drawings.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. In the drawings, the thicknesses of layers and regions may be exaggerated for clarity. Like reference numbers throughout the specification indicate like elements.

Embodiment

Method of Manufacturing Hydrogen Sensor Including Metal Nanoribbon Array Having Nanogaps The present invention provides a method of manufacturing a hydrogen sensor including a metal nanoribbon array having nanogaps. Specifically, the method includes 1) a step of forming a self-assembled single layer on a stamp substrate provided with uneven parts for pattern formation; 2) a step of forming a metal thin film layer on the self-assembled single layer; 3) a step of disposing the stamp substrate on a sensor substrate so that a polymer layer formed on the sensor substrate and the metal thin film layer are brought into contact with each other; 4) a step of transferring a metal nanoribbon array having nanogaps to the sensor substrate by performing pressure and heat treatment on the stamp substrate and removing the stamp substrate; and 5) a step of respectively forming first and second electrodes on both ends of the metal nanoribbon array.

FIGS. 1a-1f are schematic diagrams illustrating a method of manufacturing a hydrogen sensor according to one embodiment of the present invention.

Referring to (a) of FIG. 1, in Step 1 of the method of manufacturing a hydrogen sensor according to the present invention, a self-assembled single layer 50 may be formed on a stamp substrate 10 provided with uneven parts for pattern formation. The stamp substrate 10 may be provided with uneven parts for pattern formation that allow a metal thin film layer described below to have a metal ribbon array structure. Specifically, the stamp substrate 10 may be an etched substrate having a structure in which a plurality of lines are arranged in one direction on the surface of the stamp substrate 10. The lines may have any size, such as a micrometer size, a nanometer size, and the like. In particular, even when lines forming the uneven parts of the stamp substrate 10 have a micrometer size (for pitch and/or width), nanogaps having a nanometer size may be easily formed in a metal ribbon array included in a hydrogen sensor described below. Therefore, as compared with the case wherein the uneven parts of the stamp substrate 10 have a nano size, manufacturing costs may be reduced and a process of preparing the stamp substrate 10 may be simplified. The uneven parts for pattern formation may be formed on the stamp substrate 10 using a general lithography method. As the stamp substrate 10, various types of substrates may be used. For example, a silicon (Si) substrate may be used, but the present invention is not limited thereto.

The self-assembled single layer 50 may be formed of an organic compound material that can be self-assembled, and may be formed using a general organic compound deposition method. The self-assembled single layer 50 may be deposited on the uneven parts of the stamp substrate 10 to be formed with a pattern corresponding to the uneven parts. The self-assembled single layer 50 may be formed of at least one selected from tridecafluoro-1,1,2,2-tetrahydrooctyltrichlorosilane, octadecyltrichlorosilane, 3-methacryloxypropyltrimethoxysilane, and 3-aminopropyltriethoxysilane. In one embodiment of the present invention, the self-assembled single layer 50 may be formed of tridecafluoro-1,1,2,2-tetrahydrooctyltrichlorosilane. The self-assembled single layer 50 may be formed to easily transfer a metal thin film layer described below to a sensor substrate. Specifically, when pressure and heat treatment is performed on the stamp substrate 10 on which the self-assembled single layer 50 is formed, the metal thin film layer deposited inside the uneven parts (trench) of the stamp substrate 10 is transferred to the sensor substrate to easily form a metal nanoribbon array having nanogaps.

In Step 2 of the method of manufacturing a hydrogen sensor according to the present invention, a metal thin film layer may be formed on the self-assembled single layer. As shown in (b) of FIG. 1, a metal thin film layer 100 may be formed on the self-assembled single layer 50. Since the metal thin film layer 100 is deposited on the self-assembled single layer 50 deposited in an alternating pattern in the trenches of the uneven parts of the stamp substrate 10 and on upper parts (plateaus) between the trenches, the metal thin film layer 100 may have a pattern corresponding to the pattern of the self-assembled single layer 50. Specifically, the metal thin film layer 100 may be formed of any one selected from palladium (Pd), platinum (Pt), nickel (Ni), gold (Au), silver (Ag), titanium (Ti), cobalt (Co), tungsten (W), and an alloy of two or more thereof. The metal thin film layer 100 may be formed as the metal nanoribbon array of the present invention through a process described below.

The metal thin film layer 100 may be formed on the self-assembled single layer 50 using at least one method selected from electron beam evaporation, thermal evaporation, and sputtering.

The metal thin film layer 100 may be formed to have a thickness of 5 nm to 30 nm. When the thickness of the metal thin film layer 100 is less than 5 nm, since the metal thin film layer 100 is too thin, it is difficult to continuously form nanoribbons when the metal thin film layer 100 is formed into a metal nanoribbon array. When the thickness of the metal thin film layer 100 is more than 30 nm, formation of stable nanogaps may be difficult.

Referring to (c) of FIG. 1, the upper part of a sensor substrate 300 may be coated with a polymer layer 200. A flexible substrate may be used as the sensor substrate 300. For example, any one material having flexibility selected from polyethylene terephthalate (PET), polyethylene naphthalate (PEN), polyethersulfone (PES), polyimide (PI), and polyvinyl chloride (PVC) may be used to be the sensor substrate 300. Therefore, according to the above-described method, a pattern having a reverse structure with respect to the shape of the uneven parts of the stamp substrate 10 may be form on the sensor substrate 300 through a pressure and heat treatment process described below without a separate lithography process. In this case, the sensor substrate 300 may be formed of a material that may be deformed by pressure and heat treatment.

The polymer layer 200 formed on the sensor substrate 300 may serve as an adhesive layer for attaching a metal nanoribbon array to the sensor substrate 300 when the metal nanoribbon array is transferred to the sensor substrate 300. In this case, the polymer layer 200 may be formed of a thermoplastic polymer having adhesive properties. For example, the polymer layer 200 may be formed of at least one material selected from polymethyl methacrylate (PMMA), polyacrylonitrile (PAN), polyethylene oxide (PEO), and polyvinylidene difluoride (PVDF). In one embodiment of the present invention, the polymer layer 200 may be formed of polymethyl methacrylate (PMMA).

In Step 3 of the method of manufacturing a hydrogen sensor according to the present invention, a metal nanoribbon array having nanogaps may be transferred to the sensor substrate by performing pressure and heat treatment on the stamp substrate and removing the stamp substrate.

First, as shown in (c) of FIG. 1, the sensor substrate 300, the surface of which is coated with the polymer layer 200, may be prepared, and the stamp substrate 10 may be disposed on the sensor substrate 300. In this case, the two substrates may be arranged so that the polymer layer 200 formed on the sensor substrate 300 and the metal thin film layer 100 formed on the stamp substrate 10 are brought into contact with each other.

Then, the stamp substrate 10 disposed on the sensor substrate 300 may be subjected to pressure and heat treatment. Specifically, referring to (d) of FIG. 1, the inside of a reactor in which the process is performed may be maintained at a constant temperature, and pressure may be applied to the stamp substrate 10 in the direction of the sensor substrate 300 disposed under the stamp substrate 10. At this time, preferably, pressure is applied so that the pattern of the metal thin film layer 100 corresponding to the uneven parts of the stamp substrate 10 is sufficiently transferred to the polymer layer 200 located under the metal thin film layer 100. When the stamp substrate 10 is heat-treated, the temperature range may vary depending on the thermal stability of the sensor substrate 300 disposed under the stamp substrate 10.

Specifically, the stamp substrate 10 may be heat-treated at a temperature of 100° C. to 200° C. under a pressure of 100 psi to 200 psi. When the pressure applied to the stamp substrate 10 is less than 100 psi, the uneven pattern of the stamp substrate 10 may not be transferred. When the pressure applied to the stamp substrate 10 is more than 200 psi, the stamp substrate 10 and the sensor substrate 300 may be damaged and the transfer process may not be properly performed. In addition, since the polymer layer 200 is a thermoplastic polymer having flexibility at a certain temperature, when heat treatment temperature is less than 100° C., adhesion may become poor and the metal thin film layer 100 may not be separated from the stamp substrate 10. On the other hand, when heat treatment temperature is more than 200° C., the thermal stability of the sensor substrate 300 may be deteriorated and pattern transfer may not be properly performed. As shown in (d) of FIG. 1, a pattern having a reverse structure with respect to the pattern of the metal thin film layer 100 may be formed in the polymer layer 200 and a portion of the upper portion of the sensor substrate 300. In one embodiment of the present invention, when the metal nanoribbon array is transferred, the stamp substrate 10 may be subjected to heat treatment at 130° C. under a pressure of about 160 psi.

Thereafter, as shown in (e) of FIG. 1, when the stamp substrate 10 on which the self-assembled single layer 50 is formed is removed, a metal nanoribbon array 150 may be transferred onto the sensor substrate 300 on which the polymer layer 200 is formed. That is, as described above, pressure and heat treatment may be performed on the stamp substrate 10, and then the stamp substrate 10 may be removed. As a result, the metal thin film layer 100 formed on the stamp substrate 10 may be transferred onto the sensor substrate 300 in the form of the metal nanoribbon array 150 having nanogaps.

When pressure is applied to the stamp substrate 10 to transfer the metal nanoribbon array 150 onto the sensor substrate 300, a metal thin film deposited inside the pattern (that is, in the trenches) of the metal thin film layer 100 is also separated and transferred. Therefore, in the metal nanoribbon array 150 transferred onto the sensor substrate 300, as metal ribbons alternately arranged up and down are brought into close contact with each other, nanogaps, which are minute nanoscale spaces formed in a direction perpendicular to the surface of the substrate, may be formed between the adjacent metal ribbons. The width of the nanogaps may be 1 nm to 80 nm. In one embodiment of the present invention, the average width of the nanogaps may be about 40 nm. The nanogaps may be formed between the metal ribbons, and may be present in a precisely aligned form in the metal nanoribbon array 150. Due to the nanogaps, resistance between the electrodes of the hydrogen sensor becomes very large, so that the initial current value becomes small, thereby improving the sensitivity of the hydrogen sensor. In one embodiment of the present invention, palladium (Pd) may be used as a constituent material of the metal nanoribbon array 150. In this case, when palladium (Pd) is exposed to hydrogen at a specific concentration or more, opening/closing of the nanogaps in the palladium (Pd) nanoribbon array may be made possible by the expansion characteristics of the lattice. Due to opening/closing of the nanogaps, performance of the sensor may be further improved. Specifically, this will be described in detail in the following examples and drawings.

In Step 5 of the method of manufacturing a hydrogen sensor according to the present invention, first and second electrodes may be formed on both ends of the metal nanoribbon array, respectively. Specifically, referring to (f) of FIG. 1, first and second electrodes 401 and 402 may be formed on both ends of the metal nanoribbon array 150, respectively, in a direction parallel to the alignment direction of nanogaps present in the metal nanoribbon array 150. The first and second electrodes 401 and 402 may be formed using conventional electrode materials for a sensor. For example, silver (Ag) may be used, without being limited thereto.

The method of manufacturing a hydrogen sensor according to the present invention may further include a step of bending the sensor substrate upward in a convex shape. When the hydrogen sensor substrate is bent in a convex shape, the nanogaps may be expanded to reduce the initial current of the sensor, thereby further improving the sensitivity of the sensor. Specifically, when bending of the sensor substrate is performed, the bending radius may be 1 mm to 3 mm. Within this range, the initial current of the hydrogen sensor of the present invention may be lowered to about $10^{-11}$ A to $10^{-12}$ A, thereby increasing the sensitivity of the sensor. In this case, the amount of current after the nanogaps are closed upon hydrogen exposure may rapidly increase to about $10^{-4}$ A. In addition, when bending is performed to have a bending radius of 1 mm to 3 mm, since the sensor substrate is appropriately deformed, the expanded nanogaps may be maintained even when the hydrogen sensor is reopened.

As described above, according to the method of manufacturing a hydrogen sensor according to the present invention, since the metal nanoribbon array may be directly transferred to a substrate without a lithography process using an organic solvent, substrates vulnerable to organic solvents may also be used. In addition, when the metal nanoribbon array having nanogaps is applied, the hydrogen sensor may have excellent performance The hydrogen sensor is expected to be actively used in related fields. In addition, the present invention is a first example of applying a metal nanoribbon array having periodically aligned nanogaps to a hydrogen gas sensor. According to the present invention, a hydrogen sensor may be easily manufactured.

Hydrogen Sensor Including Metal Nanoribbon Array Having Nanogaps

In addition, the present invention provides a hydrogen sensor manufactured using the method of manufacturing a hydrogen sensor including a metal nanoribbon array having nanogaps.

Since the hydrogen sensor is manufactured by the method of manufacturing a hydrogen sensor described above, description of the hydrogen sensor may be the same as in the method of manufacturing a hydrogen sensor. Therefore, a detailed description of the hydrogen sensor of the present invention will be omitted, and specific configuration of the hydrogen sensor will be described below.

Specifically, the hydrogen sensor includes a substrate on which a pattern is formed; a polymer layer disposed on the substrate and having a pattern corresponding to the pattern of the substrate; a metal nanoribbon array disposed on the polymer layer and having a pattern corresponding to the pattern of the polymer layer, wherein the metal nanoribbon array has nanogaps; and first and second electrodes formed on both ends of the metal nanoribbon array, respectively. In one embodiment of the present invention, the hydrogen sensor may have a structure as shown in the schematic diagram of (f) of FIG. 1. In this case, the alignment direction of the first and second electrodes may be parallel to the alignment direction of the nanogaps.

The width of the nanogaps may be 1 nm to 80 nm. When bending of a sensor substrate is performed, the width of the nanogaps may be expanded to 150 nm. In this case, initial current may be reduced due to expansion of the nanogaps, so that sensitivity to hydrogen gas may be remarkably increased. When bending is excessively performed, nanogaps having a size of several hundred nanometers may be formed, and nanogaps expanded by expansion of the metal nanoribbons may not be filled with hydrogen gas. Accordingly, the sensor may become electrically insulated and thus performance of the sensor may not be realized.

The thickness of the metal nanoribbon array may be 5 nm to 30 nm. When the thickness of the metal nanoribbon array is less than 5 nm, nanoribbons may not be continuously formed. When the thickness of the metal nanoribbon array is more than 30 nm, nanogaps may not be stably formed.

As the width between the first and second electrodes decreases, performance may be improved in terms of sensitivity, response and recovery time. Specifically, the width between the first and second electrodes may be 200 μm to 4,000 μm. Specifically, the width between the first and second electrodes refers to a channel length, and the channel length may be easily adjusted through a shadow mask used in formation of the electrodes. Since the first and second electrodes are disposed at both ends of the metal nanoribbon array, respectively, the distance between the first and second electrodes may be related to the number of nanogaps present in the metal nanoribbon array. Specifically, this will be explained in detail through the following examples and drawings.

Hereinafter, the present invention will be described in more detail with reference to the following preferred examples. These examples are provided for illustrative purposes only and should not be construed as limiting the scope and spirit of the present invention.

Example 1

Manufacture of Hydrogen Sensor Including Metal Nanoribbon Array

Uneven parts having a diffraction grating pattern, in which a plurality of nanolines having a pitch of 1.5 μm, a line width of 650 nm, and a height of 450 nm were periodically arranged, were formed in a silicon (Si) stamp substrate using helium (He)-cadmium (Cd) laser (wavelength=325 nm) interference lithography.

The stamp substrate was coated with tridecafluoro-1,1,2,2-tetrahydrooctyltrichlorosilane ($CF_3(CF_2)_5(CH_2)_2SiCl_3$) to form a self-assembled single layer. Then, a palladium (Pd) thin film layer was formed on the self-assembled single layer in the thicknesses of 5 nm, 10 nm, and 30 nm for each sample using an electron beam evaporator.

In addition, a polyethylene terephthalate (PET) substrate was coated with 4% polymethyl methacrylate (PMMA) diluted with chlorobenzene to have a coating thickness of 240 nm using spin coating. Thereafter, the silicon stamp substrate was disposed on the PET substrate so that the PMMA layer and the palladium thin film layer were brought into contact with each other. Then, to achieve conformal contact between the palladium thin film layer and the PET substrate on which the PMMA layer was formed, the internal temperature of a reactor was raised to 130° C., and a pressure of 160 psi was applied to the stamp substrate for about 10 minutes in the direction from the stamp substrate to the PET substrate, and then the internal temperature of the reactor was slowly cooled to about 90° C. After heat and pressure treatment, the stamp substrate was separated. Through the process, a palladium nanoribbon array was transferred onto the PET substrate on which the PMMA layer was formed. Thereafter, silver (Ag) electrodes (electrodes A) were deposited with a thickness of 60 nm on both ends of the palladium nanoribbon array in the direction parallel to the alignment direction of the nanogaps using evaporation. When the electrodes were formed, the width of the palladium nanoribbon array used as a channel between the electrodes was varied to 200 μm, 700 μm, or 4,000 μm, and thus the samples were classified by width.

Comparative Example 1

Electrodes (Electrodes B) Arranged in Direction Perpendicular to Alignment Direction of Nanogaps A hydrogen sensor was manufactured in the same manner as in Example 1 except that electrodes were arranged in a direction perpendicular to the alignment direction of the nanogaps.

FIGS. 2a-2b show the structural formula and an SEM image of a self-assembled single layer made of trideca-fluoro-1,1,2,2-tetrahydrooctyltrichlorosilane formed on a stamp substrate, respectively.

Figure 2:
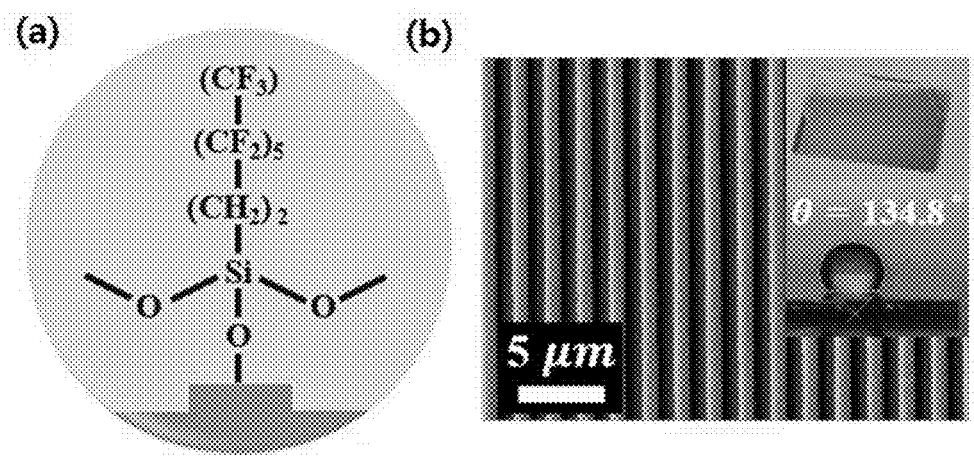
FIGS. 2a-2b are the structural formula and an SEM image of a self-assembled single layer formed on a stamp substrate, respectively.

Referring to FIGS. 2, the surface of the self-assembled single layer formed on the stamp substrate exhibits a contact angle of 134.8°, indicating that the surface is thermodynamically stable. From this result, using the method of the present invention, it can be seen that the surface of the silicon stamp substrate does not react with other substances or no absorption of other substances occurs on the surface of the silicon stamp substrate. Therefore, according to the present invention, a self-assembled single layer is formed on a stamp substrate, so that a metal thin film layer formed on the stamp substrate may be easily transferred in the form of a metal nanoribbon array to a sensor substrate. Thus, the process yield may be improved.

FIGS. 3a-3f include SEM images of the palladium nanoribbon array manufactured in Example 1 and graphs showing a histogram plot of the nanogaps of the palladium nanoribbon array and photoelectron spectroscopy (XPS) and X-ray diffraction analysis (XRD) results of the palladium nanoribbon array.

Figure 3:
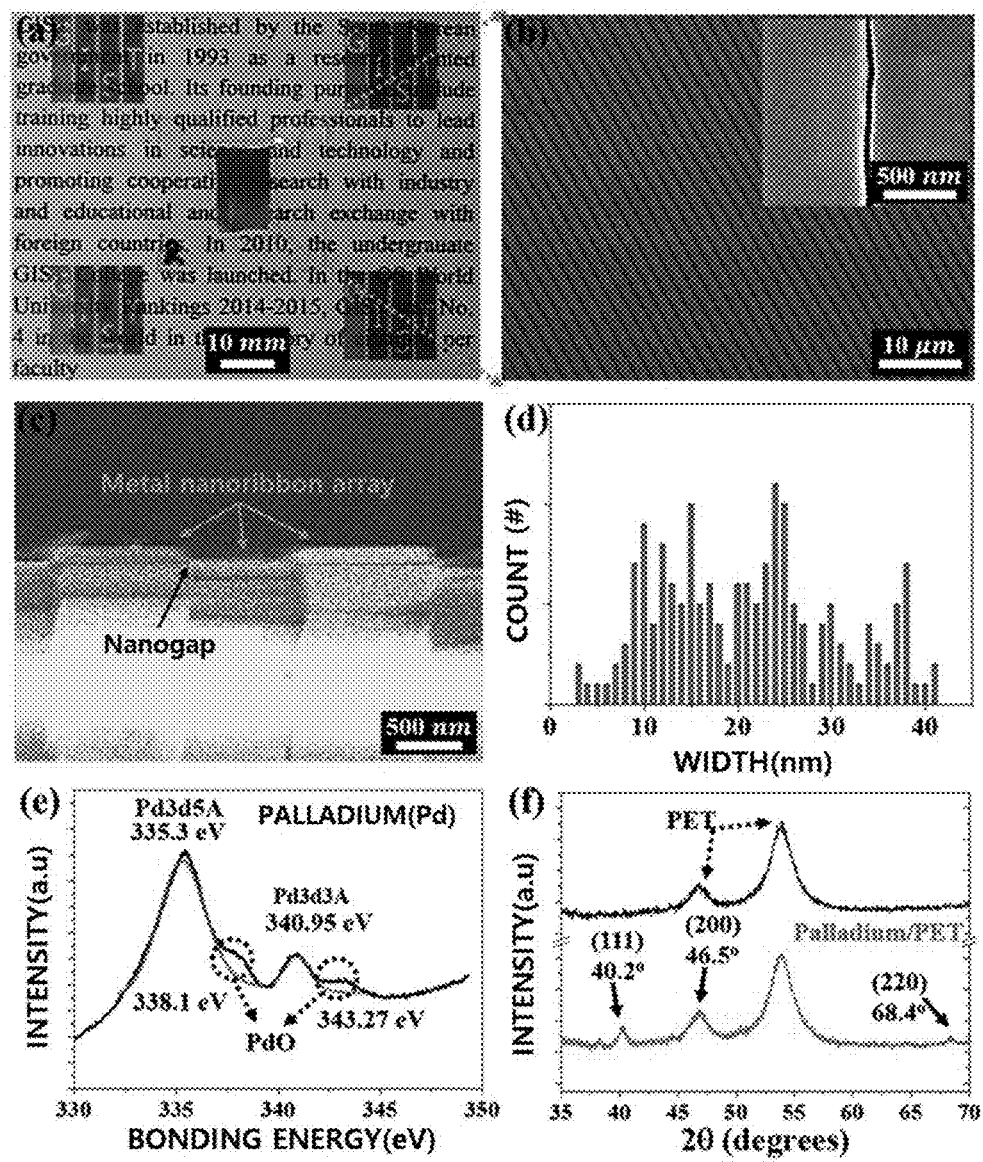
FIGS. 3a-3f are SEM images of the palladium nanoribbon array manufactured in Example 1 and graphs showing a histogram plot of the nanogaps of the palladium nanoribbon array and photoelectron spectroscopy (XPS) and X-ray diffraction analysis (XRD) results of the palladium nanoribbon array.

In (a) of FIG. 3, an actual image of a palladium nanoribbon array formed on the PET substrate manufactured in Example 1 is shown. It can be seen that the opaque palladium nanoribbon array having a size of about 1.5 cm$^2$ is closely formed on the PET substrate. Referring to (b) of FIG. 3, which shows an enlarged image of the palladium nanoribbon array, nanoribbons constituting the continuous palladium nanoribbon array are arranged adjacent to each other with a width of 650 nm to 850 nm. In addition, between the nanoribbons, as shown in the upper right image, nanoscale spaces (i.e., nanogaps) are present.

Referring to (c) of FIG. 3, it can be seen that the palladium nanoribbon array has a relatively flat surface and a structure in which a plurality of nanoribbons are alternately arranged up and down. Specifically, nanoribbons disposed on the upper side are transferred from a palladium thin film layer deposited in trenches (i.e., spaces between the uneven parts of a stamp substrate), and nanoribbons disposed on the lower side are transferred from a palladium thin film layer deposited on the upper portions of the uneven parts of the stamp substrate.

As described above, according to the present invention, when a metal nanoribbon array is transferred, temperature and pressure treatment is performed on a stamp substrate to strongly press a polymer layer and a sensor substrate with the stamp substrate, so that a metal thin film layer deposited inside uneven parts (i.e., in etched deep regions) provided on the stamp substrate is also transferred to a sensor substrate. In this case, the metal nanoribbons of the metal nanoribbon array transferred onto the sensor substrate are brought into close contact with each other, and nanogaps having a width of about 40 nm or less may be precisely arranged throughout the metal nanoribbon array.

In (d) of FIG. 3, a graph showing histogram plot results depending on the width distribution of nanogaps is shown. The analysis was performed on 15 different regions among 200 or more nanogaps. Referring to (d) of FIG. 3, it can be seen that the width of the nanogaps is mainly in the range of 10 nm to 30 nm, and in some cases, nanoribbons making up the metal nanoribbon array are not completely separated from the neighboring nanoribbons and are loosely connected to each other.

In (e) of FIG. 3, x-ray photoelectron spectroscopy (XPS) analysis results for confirming the presence of the palladium element is shown. It can be seen that the typical dual peaks corresponding to the palladium element, Pd3d5A and Pd3d3A, appear at binding energies of 335.3 eV and 340.95 eV, respectively. In addition, peaks at binding energies of 338.1 eV and 343.27 eV adjacent to the peaks of palladium element may be attributed to palladium oxide.

In (f) of FIG. 3, X-ray diffraction (XRD) results for confirming the presence of the palladium element is shown. It can be seen that three typical diffraction peaks corresponding to the (111) plane, the (200) plane, and the (220) plane in the face-centered cubic lattice of palladium are respectively observed at 2θ values of 40.2°, 46.5°, and 68.4°. However, it can be seen that the diffraction peak of the (200) plane is not clearly distinguished due to overlap with the relatively strong peak of the PET substrate used as the sensor substrate.

Measurement of Hydrogen Sensing Characteristics

Hydrogen gas sensing was performed inside a quartz tube connected to a semiconductor parameter analyzer (Keithley 2400S). First, high-purity air having a purity of 99.999% was introduced into the quartz tube to stabilize the level of initial current (base current) while eliminating other reaction gases. After the initial current level reached a stable level, the hydrogen sensors of Example 1 and Comparative Example 1 were exposed to various concentrations of hydrogen gas under a humidity of about 30% at room temperature. At this time, three types of sensors having channel lengths (widths between electrodes) of 200 μm, 780 μm, and 4,000 μm, respectively, were used as measurement sensors. Sensor recovery time was measured under a continuous air flow of 3,000 sccm with the hydrogen valve closed.

FIGS. 4a-4c include an image showing the arrangement direction of electrodes of the hydrogen sensor manufactured in Example 1, and graphs showing the sensitivity and changes in the response time and in the recovery time of the sensor depending on channel length, respectively.

Figure 4:
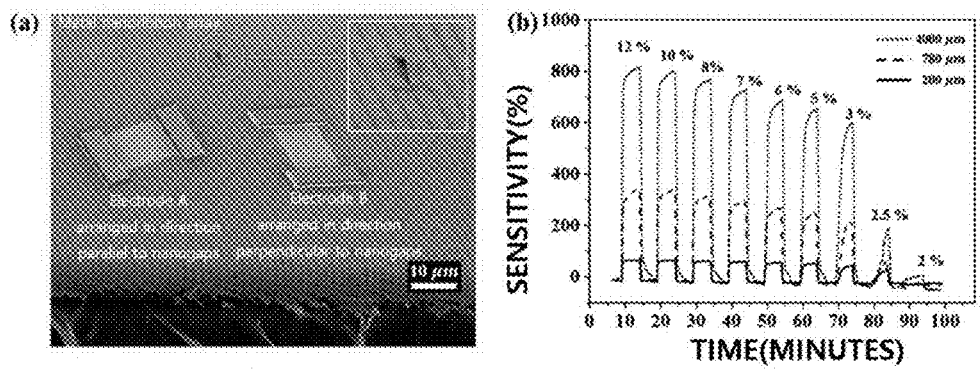
FIGS. 4a-4c include an image showing the arrangement direction of electrodes of the hydrogen sensor manufactured in Example 1, and graphs showing the sensitivity and changes in the response time and in the recovery time of the sensor depending on channel length, respectively.
Figure 4:
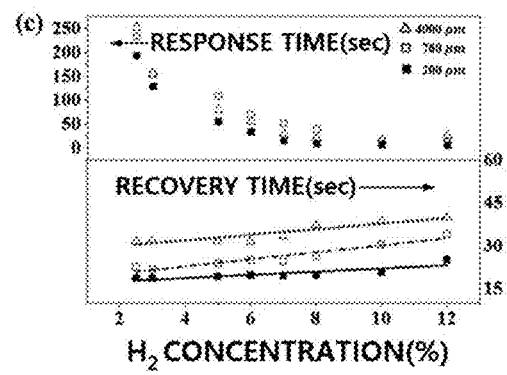

First, in (a) of FIG. 4, the sensor of Example 1 includes electrodes A arranged in a direction parallel to the alignment direction of nanogaps and the sensor of Comparative Example 1 includes electrodes B arranged in a direction perpendicular to the alignment direction of nanogaps. First, in the case of the sensor including electrodes A, metal nanoribbons are aligned toward electrodes, and nanogaps are arranged perpendicular to the electrical conduction path.

Therefore, the sensor including electrodes A is suitable for the hydrogen-induced lattice expansion (HILE) mechanism for hydrogen gas detection. In this case, when hydrogen gas is adsorbed, the nanogaps are closed by expansion, and the amount of current may be remarkably increased. On the other hand, in the case of the sensor including electrodes B, palladium nanoribbons are aligned in the electrical conduction path, and thus current flows through continuously formed palladium nanoribbons. Therefore, when the sensor is exposed to hydrogen gas, resistance is increased and the amount of current is reduced due to PdHx formed along the continuously formed palladium nanoribbons. As shown in the embedded image in the upper right of (a) of FIG. 4, it can be seen that one of nanoribbons arranged in the metal nanoribbon array is separated from the substrate and folded without affecting the neighboring nanoribbons. From these results, it can be seen that the metal nanoribbon array of the present invention is separated by the nanogaps.

In (b) of FIG. 4, a graph shows the sensitivities of three sensors having different channel lengths under various hydrogen concentrations of 12%, 10%, 8%, 7%, 6%, 5%, 3%, 2.5%, and 2%. In this case, a sensor substrate was manufactured without a bending process. The sensitivity (S) was calculated by the following equation: S (%) 32 $[(I_s-I_i)/I_i] \times 100$. In the equation, $I_s$ represents saturated current in air containing hydrogen gas, and $I_i$ represents initial current in each sensing cycle.

Specifically, referring to (b) of FIG. 4, the sensor having a channel length of 4,000 μm exhibits the highest sensitivity at all hydrogen concentrations, and especially at a hydrogen concentration of 12%, the sensitivity of the sensor reaches up to 800% or more. In addition, all sensors exhibit significantly lower sensitivity at a hydrogen concentration of 2.5%. From these results, it can be seen that palladium constituting the nanoribbon array did not expand to the proper volume due to an insufficient hydrogen concentration. In addition, it can be seen that, since the sensors having channel lengths of 780 μm and 200 μm have a higher initial current level than that of the sensor having a channel length of 4,000 μm, the sensors having channel lengths of 780 μm and 200 μm exhibit relatively low sensitivity. It is considered that these results are obtained because the saturation current levels of the three sensors are similar when exposed to hydrogen gas.

In addition, considering the pitch size, it can be seen that the sensors having a channel length of 4,000 μm, 780 μm, and 200 μm, respectively, have 2666, 520, and 133 nanogaps, respectively. The channel lengths (widths between electrodes) may be adjusted through a shadow mask, and the channel length adjustment is related to adjustment of the number of nanogaps. That is, according to the present invention, the initial current value of the sensing channel of the hydrogen sensor may be easily controlled by adjusting the number of nanogaps.

In (c) of FIG. 4, a graph shows the response time and recovery time of the three sensors at each hydrogen concentration. Referring to (c) of FIG. 4, as the concentration of hydrogen gas increases, the response time exponentially decreases, and the recovery time linearly increases. These results suggest that the nanogaps rapidly close due to rapid expansion of the lattice at high hydrogen concentration, resulting in an exponential decrease in response time. In addition, it is considered that the recovery time is prolonged under high hydrogen concentration since it takes time to desorb relatively abundant adsorbed hydrogen to shrink the metal nanoribbons. In particular, since a sensor having a channel length of 200 μm includes relatively few nanogaps, the sensor exhibits the fastest response and recovery behavior at all concentrations. Thus, since repetitive filling and opening/closing may be performed during circulation operation, the sensor may be used for a long period of time while maintaining the performance of the sensor.

Example 2

Bending Hydrogen Sensor in Convex Shape

The sensor substrate of the hydrogen sensor manufactured in Example 1 was subjected to bending treatment so that the sensor substrate was bent upward in a convex shape.

Comparative Example 2

Bending Hydrogen Sensor in Concave Shape

The sensor substrate of the hydrogen sensor manufactured in Example 1 was subjected to bending treatment so that the sensor substrate was bent downward in a concave shape.

FIGS. 5a-5b include images and a graph showing the characteristics of the hydrogen sensors according to Example 2 and Comparative Example 2 depending on bending treatment and bending radii.

Figure 5:
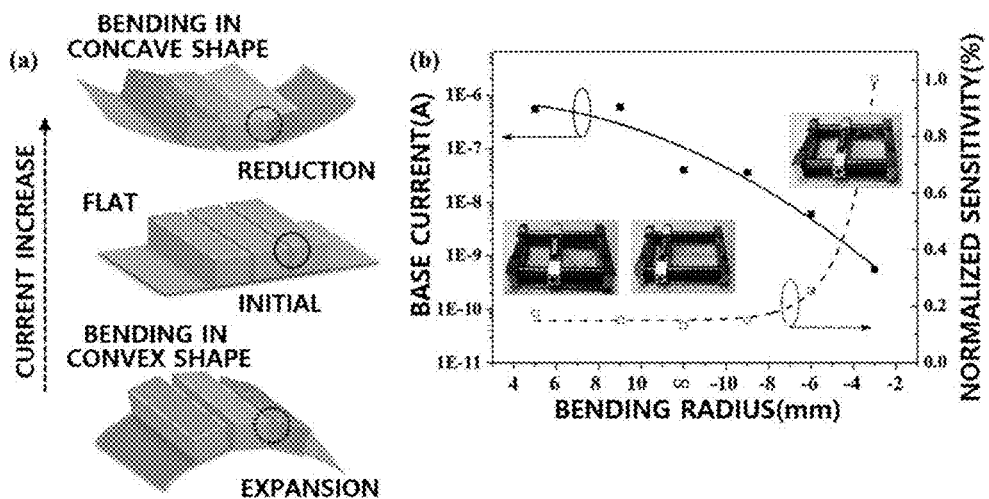
FIGS. 5a-5b include images and a graph showing the characteristics of the hydrogen sensors according to Example 2 and Comparative Example 2 depending on bending treatment and bending radii.

Referring to (a) of FIG. 5, by the concave-shape bending described in Comparative Example 2, the width of nanogaps included in the metal nanoribbon array of the sensor is reduced. In addition, by the convex-shape bending described in Example 2, the width of nanogaps is increased. Specifically, referring to (b) of FIG. 5, when the sensor substrate was bent in a convex shape having a bending radius of 3 mm, the level of initial current was decreased to $10^{-10}$ A from the case without bending treatment (current level: $10^{-8}$ A). These results suggest that, when the sensor is bent in a convex shape, loosely connected neighboring metal nanoribbons are completely separated and the width of nanogaps is increased to 150 nm, resulting in a decrease in the initial current level. In addition, it can be seen that the sensitivity is also much improved when the sensor is bent in a convex shape.

On the other hand, in the case of the sensor bent in a concave shape, it can be seen that adjacent metal nanoribbons are connected to each other due to reduction in the width of nanogaps, thereby increasing the initial current level to $10^{-7}$ A. As described above, according to the present invention, the performance of the sensor may be further improved by convex-shape bending.

FIGS. 6a-6c include graphs showing electrical characteristics according to repeated operation of a sensor, sensitivity with or without bending treatment, and changes in response time and recovery time, respectively.

Figure 6:
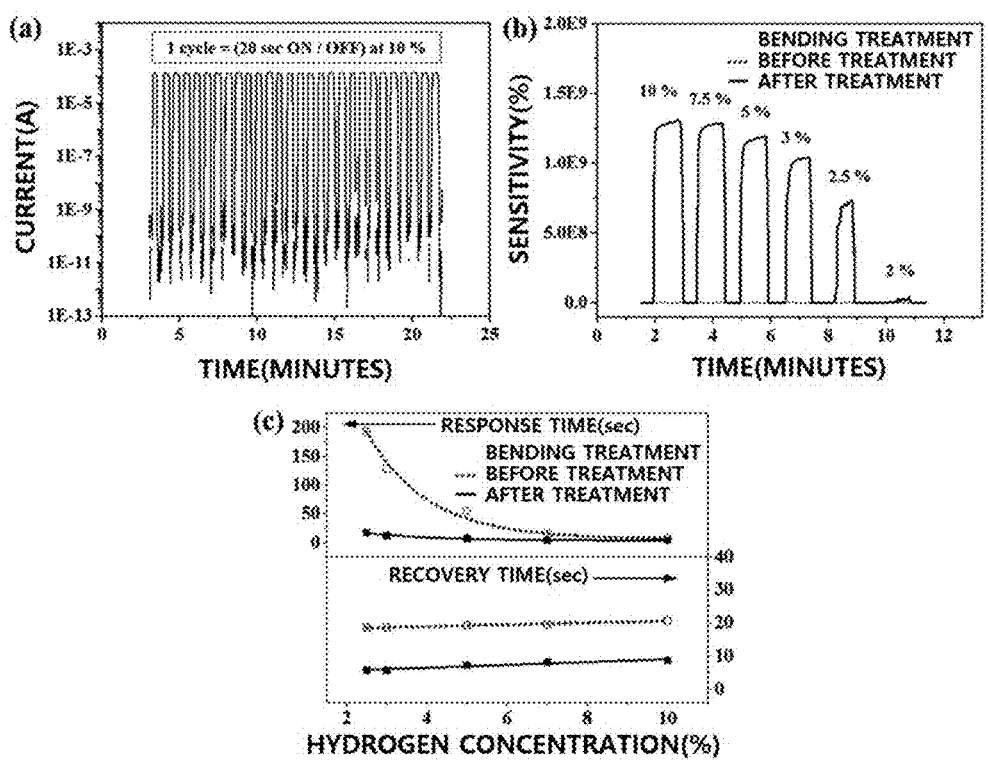
FIGS. 6a-6c include graphs showing the sensitivity and recovery characteristics of a sensor according to repeated operation of the sensor and bending treatment.

In (a) of FIG. 6, a graph shows the sensing performance of a sensor having a channel length of 200 μm when the sensor operates according to the condition that the cycle of maintaining the 'on' state for 20 seconds and maintaining the 'off' state for 20 seconds is repeatedly performed at an operating power of 1.2 μW under a 10% hydrogen concentration. Regarding (a) of FIG. 6, the 'on' current at 0.01 V is $10^{-4}$ A. When hydrogen gas is shut off, the initial current is recovered from $10^{-11}$ A to $10^{-12}$ A. Rapid response is also observed despite repeated on/off. These results indicate that the sensor has excellent repeatability. Although not shown in (a) of FIG. 6, the hydrogen sensor of the present invention exhibited excellent performance even after performing 100 cycles.

In (b) of FIG. 6, a graph shows the sensitivity of a sensor having a channel length of 200 μm before and after bending treatment for forming a convex shape at various hydrogen concentrations. Referring to (b) of FIG. 6, it can be seen that the sensitivity of the sensor is considerably increased after the bending treatment. These results may be attributed to reduction of the initial current due to an increase in the width of nanogaps due to bending treatment for forming a convex shape. In addition, sensitivity may also be affected by increasing saturated current by reducing the number of nanogaps in a channel Referring to (c) of FIG. 6, it can be seen that, after bending treatment, the response time of the sensor is shortened from 6.9 seconds to 3.6 seconds, and the recovery time is also shortened from 20.7 seconds to 8.7 seconds.

Meanwhile, embodiments of the present invention disclosed in the present specification and drawings are only provided to help understanding of the present invention and the present invention is not limited to the embodiments. It will be apparent to those skilled in the art that various modifications can be made to the above-described exemplary embodiments of the present invention without departing from the spirit or scope of the invention.

The invention claimed is:

1. A hydrogen sensor, comprising:
a substrate on which a pattern is formed;
a polymer layer disposed on the substrate and having a pattern corresponding to the pattern of the substrate;
a metal nanoribbon array disposed on the polymer layer and having a pattern corresponding to the pattern of the polymer layer, wherein the metal nanoribbon array has nanogaps; and
first and second electrodes formed on both ends of the metal nanoribbon array, respectively.

2. The hydrogen sensor according to claim 1, wherein the first and second electrodes are arranged in a direction parallel to an alignment direction of the nanogaps.

3. The hydrogen sensor according to claim 1, wherein the nanogaps have a width of 1 nm to 80 nm.

4. The hydrogen sensor according to claim 1, wherein the metal nanoribbon array has a thickness of 5 nm to 30 nm.

5. The hydrogen sensor according to claim 1, wherein width between the first and second electrodes is 200 μm to 4,000 μm.

6. The hydrogen sensor according to claim 1, wherein the sensor substrate is subjected to a bending process so that the sensor substrate is bent upward in a convex shape.

7. A method of manufacturing a hydrogen sensor, comprising:
a step of forming a self-assembled single layer on a stamp substrate provided with uneven parts for pattern formation;
a step of forming a metal thin film layer on the self-assembled single layer which is formed on the uneven parts;
a step of disposing the stamp substrate on a sensor substrate so that a polymer layer formed on the sensor substrate and the metal thin film layer are brought into contact with each other;
a step of transferring a metal nanoribbon array having nanogaps to the sensor substrate by performing pressure and heat treatment on the stamp substrate to transfer the metal thin film layer formed on the uneven parts and removing the stamp substrate, so that the metal nanoribbon array is transferred from the metal thin film formed in trenches of the uneven parts and the metal thin film formed in upper parts between the trenches; and
a step of respectively forming first and second electrodes on both ends of the metal nanoribbon array,
wherein the metal nanoribbon array has metal ribbons alternately arranged up and down, and has the nanogaps that are spaces formed between a metal ribbon transferred from the metal thin film layer formed in the trench of the uneven parts and a metal ribbon transferred from the upper part of the uneven parts.

8. The method according to claim 7, wherein the self-assembled single layer is formed of at least one material selected from tridecafluoro-1,1,2,2-tetrahydrooctyltrichlorosilane, octadecyltrichlorosilane, 3-methacryloxypropyltrimethoxysilane, and 3-aminopropyltriethoxysilane.

9. The method according to claim 7, wherein the metal thin film layer is formed of any one selected from palladium (Pd), platinum (Pt), nickel (Ni), gold (Au), silver (Ag), titanium (Ti), cobalt (Co), tungsten (W), and an alloy of two or more thereof.

10. The method according to claim 7, wherein the metal thin film layer is formed using at least one method selected from electron beam evaporation, thermal evaporation, and sputtering.

11. The method according to claim 7, wherein the metal thin film layer is formed to have a thickness of 5 nm to 30 nm.

12. The method according to claim 7, wherein any one material having flexibility selected from polyethylene terephthalate (PET), polyethylene naphthalate (PEN), polyethersulfone (PES), polyimide (PI), and polyvinyl chloride (PVC) is used to form the sensor substrate.

13. The method according to claim 7, wherein the polymer layer formed on the sensor substrate comprises at least one material selected from polymethyl methacrylate (PMMA), polyacrylonitrile (PAN), polyethylene oxide (PEO), and polyvinylidene difluoride (PVDF).

14. The method according to claim 7, wherein, when the metal nanoribbon array is transferred, the stamp substrate is heat-treated at a temperature of 100° C. to 200° C. under a pressure of 100 psi to 200 psi.

15. The method according to claim 7, wherein the first and second electrodes are formed in parallel with an alignment direction of the nanogaps.

16. The method according to claim 7, further comprising a step of bending the sensor substrate upward in a convex shape.

17. The method according to claim 16, wherein, when the bending process is performed, the sensor substrate is bent to have a bending radius of 1 mm to 3 mm.

* * * * *